(12) United States Patent
Kim et al.

(10) Patent No.: US 9,937,210 B2
(45) Date of Patent: Apr. 10, 2018

(54) METHOD FOR ISOLATING FRACTION HAVING ANTI-INFLAMMATORY OR OSTEOARTHRITIS-INHIBITING EFFECTS BY USING OYSTER SHELL CHIPS

(71) Applicant: Seojin Biotech Co., Ltd., Suwon-si, Gyeonggi-do (KR)

(72) Inventors: Hak-Ju Kim, Busan (KR); Ji-Sook Han, Busan (KR); Yeoun-Ju Byoun, Seoul (KR)

(73) Assignee: Seojin Biotech Co., Ltd., Suwon-si (KR)

( * ) Notice: Subject to any disclaimer, the term of this patent is extended or adjusted under 35 U.S.C. 154(b) by 406 days.

(21) Appl. No.: 14/429,321

(22) PCT Filed: Dec. 17, 2012

(86) PCT No.: PCT/KR2012/010985
§ 371 (c)(1),
(2) Date: Mar. 18, 2015

(87) PCT Pub. No.: WO2014/046345
PCT Pub. Date: Mar. 27, 2014

(65) Prior Publication Data
US 2015/0238542 A1    Aug. 27, 2015

(51) Int. Cl.
*A61K 35/56* (2015.01)
*A61K 35/12* (2015.01)
*A61K 35/618* (2015.01)
*B01D 21/26* (2006.01)
*B01D 61/14* (2006.01)

(52) U.S. Cl.
CPC .......... *A61K 35/618* (2013.01); *B01D 21/262* (2013.01); *B01D 61/145* (2013.01)

(58) Field of Classification Search
None
See application file for complete search history.

(56) References Cited

U.S. PATENT DOCUMENTS 5,145,448 A * 9/1992 Ebisuzaki ............ A22C 29/046
452/13
5,393,553 A * 2/1995 Ando ..................... A23B 4/033
426/471

FOREIGN PATENT DOCUMENTS

| KR | 10-0173556 | 2/1999 |
| KR | 10-2008-0108738 | 12/2008 |
| KR | 10-2009-0111987 | 10/2009 |
| KR | 10-2010-0005861 | 1/2010 |
| WO | WO 2014/046345 | 3/2014 |

OTHER PUBLICATIONS

International Search Report dated May 31, 2013 From the Korean Intellectual Property Office Re. Application No. PCT/KR2012/010985 and Its Translation Into English.
Park et al. "Inhibitory Effect of Oyster Conchioloin on Pro-Inflammatory Mediator in Lipopolysaccharide—Activated Raw 264.7 Cells", Korean Journal of Oriental Physiology & Pathology, 22(4): 878-883, 2008. Abstract, Instruction, p. 879, Discussion.
Tak "Development of the High Efficient Purification Process for Conchiolin From Mollusk Shells and Its Characterization of Biological Activity", Thesis Submitted for the Fufillment of Doctor of Engineering, Department of Technology and Bioengineering, The Graduate School, Pukyong National University, Korea, p. 1-111, Feb. 26, 2008. English Abstract on p. 9. p. 17-18.

* cited by examiner

*Primary Examiner* — Chris R Tate
*Assistant Examiner* — Randall Winston (57) ABSTRACT

The present invention relates to a method for isolating a fraction having anti-inflammatory or osteoarthritis-inhibiting effects by removing impurities and washing oyster shells, which are produced during a process of producing oysters, drying same, forming a powder from the oyster shells, and adding anhydrous citric acid to same for a reaction, obtaining a reaction product, and isolating a supernatant, which is obtained by centrifugally separating the reaction product, by means of ultrafiltration. By adding the anhydrous citric acid to the oyster shell chips for the reaction at a relatively low temperature, the present invention provides superior advantages, such as significantly reducing energy costs and isolating the fraction having the anti-inflammatory or osteoarthritis inhibiting effects through a simple method.

5 Claims, 6 Drawing Sheets

METHOD FOR ISOLATING FRACTION HAVING ANTI-INFLAMMATORY OR OSTEOARTHRITIS-INHIBITING EFFECTS BY USING OYSTER SHELL CHIPS

RELATED APPLICATIONS

This application is a National Phase of PCT Patent Application No. PCT/KR2012/010985 having International filing date of Dec. 17, 2012, which claims the benefit of priority of Korean Patent Application No. 10-2012-0103334 filed on Sep. 18, 2012. The contents of the above applications are all incorporated by reference as if fully set forth herein in their entirety.

FIELD AND BACKGROUND OF THE INVENTION

The present invention relates to a method for isolating a fraction having anti-inflammatory or osteoarthritis-inhibiting effects using oyster shell. More particularly, the present invention relates to a method for isolating a fraction having anti-inflammatory or osteoarthritis-inhibiting effects which comprises removing foreign materials attached to the oyster shell, washing the oyster shell with water and then drying the washed oyster to make a powder, reacting the powder with anhydrous citric acid to obtain a reaction product, centrifuging the reaction product to obtain a supernatant and then subjecting to ultra-filtration. Since the reaction between oyster shell and anhydrous citric acid occurs at a relatively low temperature, the energy cost can be reduced and a fraction having anti-inflammatory or osteoarthritis-inhibiting effects can be isolated in a relatively simple way.

In Korea, about nine hundred thousand tons of oyster shells are produced a year, of which it is estimated that seven hundred thousand tons are discarded. The discarding of oyster shells has emerged as a serious pollution problem and has come under economic scrutiny. The main component of oyster shells is calcium carbonate ($CaCO_3$) which comprises about 95% of the oyster shell. Magnesium carbonate ($MgCO_3$) and calcium sulfate ($CaSO_4$) are also present in small quantities. The oyster shell is used as a raw material in, for example, various fillers, paper coating agents, pigments, cosmetics and pharmaceuticals, and it is even used in the manufacture of calcium carbonate ($CaCO_3$). In Japan, studies to utilize the oyster shell as a soft ground improving material and a sand pile material have been performed. In Korea, attempts to increase the recycling of oyster shells in calcium plants and fertilizer plants have been made, but an appropriate treatment plan has not yet been suggested.

On the other hand, inflammation in a living body or tissue is caused by a series of reactions which are induced by a number of stimulus such as infectious agents, ischemia, antigen-antibody reactions, heat, or physical injury. The inflammation reaction is known to display clinical symptoms such as erythema, edema, tenderness and pain. Arachidonic acid produces a variety of prostaglandins which play an important role in in vivo inflammation delivery by cyclo-oxygenase (COX), and a thromboxane involved in platelet aggregation. The COX enzyme is composed of COX-1 enzymes which plays an important role in maintaining homeostasis in normal tissues, and COX-2 enzymes, which are inducible enzymes whose expression is increased temporarily by inflammation. COX-1 enzymes are enzymes used in the production of a material (thromboxan A2) which coagulates blood, prevents blood circulation and constricts blood vessels, and are also enzymes used in the production of a mucous membrane-protecting material that functions to prevent destruction of the gastric mucous membrane.

On the other hand, COX-2 (type 2; induced form) enzymes are mainly found in the brain and kidney, and may also be found even in inflammatory cells. Particularly, COX-2 is known to be derived from the site of inflammation. COX-2 enzymes are enzymes used for generating Prostaglandin E2, a material that causes inflammation. They are also known as enzymes which promote production of Prostaglandin I2, a material that functions to prevent thrombosis and extend the blood vessel.

Inflammatory response is a mechanism for restoring and regenerating a site injured by invasiveness which gives rise to an organic lesion caused by a physical action or a chemical substance or a bacterial infection. Once the stimulus has been topically applied, substances active in blood vessels such as histamine, serotonine, bradykinin, prostaglandins, hydroxyl-eicosatetraenoic acid (HETE), and leuko-triene are isolated to induce inflammation while increasing vascular permeability. Moderate inflammation that occurs quickly following an injury is a normal reaction to quickly regenerate the injured site.

However, a long-term persistent inflammatory response may have difficulty in regenerating the injured site and can cause harm to the surrounding cells, thereby lowering a defensive power to the peripheral tissue and worsening the symptoms. Furthermore, a long-term persistent inflammatory response causes a sustained damage to the surrounding tissues. As a result, some types of inflammatory response may cause diseases such as cancer.

Thus, a tissue showing inflammation response would need to be treated with appropriate anti-inflammatory agents so that the regeneration process is completed in a short amount of time. However, topical steroids which are used to treat inflammatory diseases exhibit several side effects and so the use thereof is limited. The development of anti-inflammatory drugs having excellent efficacy and few side effects is urgently required (see Miller M. J. et al., Mediators of Inflammation, 4, pp 387-396. 1995: Appleton L. et al., Adv Pharmacol., 35, pp 27-28, 1996).

Further, recently, as Korea develops into an aging society, it has been shown that about 80% over 55 and all of those over 75 have osteoarthritis diseases. Especially, knee osteoarthritis is a disease having high societal costs such as treatment expenses as well as social activity impairment in an aging population, because the incidence is very high and sustained inflammations can induce peripheral muscle atrophy, thus causing abnormalities in the joints.

Osteoarthritis (degenerative arthritis) is a disease afflicting seniors which is frequently observed clinically, and the lesions thereof develop as a result of degeneration of the joint cartilage, and pain and swelling, joint stiffness and progressive movement disorders occur upon exercise. In osteoarthritis, inflammatory mediators such as cytokines are known to be involved in the degeneration of matrix components of joint cartilage tissue (see Pelletier et al, 1993). In particular, interleukin-1β (IL-1β) is widely accepted as one of the important pro-inflammatory cytokines which are involved in pathophysiology of the osteoarthritis (see Dinarello et al., 1988). This induces a sequential catabolism in chondro site including the up-regulation of COX gene and the release of prostaglandin E2 (see Stichtenoth et al, 2001).

Even though a non-steroidal anti-inflammatory drug during such pharmacological treatment has serious side effects, it is one of the most widely prescribed types of drugs for osteoarthritis for the long-term administration (see Abramson et al, 2003). However, recently, in order to develop strategies to prevent the onset and progress of osteoarthritis, new research and efforts have been steadily performed.

SUMMARY OF THE INVENTION

The present inventors have found that energy cost can be innovatively reduced by the reaction of an oyster shell and an anhydrous citric acid at a relatively low temperature, unlike prior arts, and a fraction having anti-inflammatory or osteoarthritis-inhibiting effects can be isolated in a simple way from a supernatant obtained by centrifuging the reaction product, thereby completing the present invention.

The present invention provides a method for isolating a fraction having anti-inflammatory or osteoarthritis-inhibiting effects which comprises reacting an oyster shell with an anhydrous citric acid at a relatively low temperature to obtain a reaction product, centrifuging the reaction product to obtain a supernatant and then subjecting to ultra-filtration. The object of the invention is to provide a method wherein energy cost can be reduced by the reaction of an oyster shell and an anhydrous citric acid at a relatively low temperature and a fraction having anti-inflammatory or osteoarthritis-inhibiting effects can be isolated in a simple way.

The present invention provides a method for isolating a fraction having an anti-inflammatory effect using oyster shell, characterized in that the said method comprises:

1) a preliminary step of removing a debris attached to the oyster shell, washing the oyster shell with water and then drying and grinding the washed oyster shell to make a powder;

2) a reaction step of reacting the oyster shell powder obtained from the said preliminary step with an anhydrous citric acid to obtain a reaction product;

3) a supernatant-recovering step of centrifuging the reaction product obtained from the said reaction step to recover a supernatant; and 4) an isolation step of isolating the supernatant obtained from the said supernatant-recovering step using an ultra-filtration membrane and then drying the same to isolate a fraction having an anti-inflammatory effect.

Also, the present invention provides a method for isolating a fraction having an anti-inflammatory effect using oyster shell, characterized by adding an anhydrous citric acid to the oyster shell powder during the reaction step in a ratio of 1:0.1921~1.9212 parts by weight and conducting the reaction at 4~100° C. for 1~24 hours.

Furthermore, the present invention provides a method for isolating a fraction having an anti-inflammatory effect using oyster shell, characterized in that the ultra-filtration membrane has a size of 10 kDa during the said supernatant-recovering step.

Further, the present invention provides a method for isolating a fraction having an anti-inflammatory effect using oyster shell, characterized in that the ultra-filtration membrane has a size of 3 kDa during the said supernatant-recovering step.

Further, the present invention provides a fraction having an anti-inflammatory effect using oyster shell, characterized in that the fraction is obtained by any one of the above isolation methods.

Further, the present invention provides a method for isolating a fraction having an osteoarthritis-inhibiting effect using oyster shell, characterized in that the said method comprises:

1) a preliminary step of removing foreign materials attached to the oyster shell, washing the oyster shell with water and then drying and grinding the washed oyster same to make a powder;

2) a reaction step of adding an anhydrous citric acid to the oyster shell powder obtained from the said preliminary step in a ratio of 1:0.1921~1.9212 parts by weight and conducting the reaction at 4~100° C. for 1~24 hours;

3) a supernatant-recovering step of centrifuging the reaction product obtained from the said reaction step to recover a supernatant; and 4) an isolation step of isolating the supernatant obtained from the said supernatant-recovering step using an ultra-filtration membrane having a size of 3 kDa and then drying the same to isolate a fraction having an osteoarthritis-inhibiting effect.

Finally, the present invention provides a method for isolating a fraction having an osteoarthritis-inhibiting effect using oyster shell, characterized in that the fraction is obtained by the said isolation method.

The method for isolating a fraction having anti-inflammatory or osteoarthritis-inhibiting effects using oyster shell in accordance with the present invention has the following advantageous effects.

First, energy cost can be innovatively reduced by adding and reacting the anhydrous citric acid to the oyster shell at a relatively low temperature.

Second, the fraction having anti-inflammatory or osteoarthritis-inhibiting effects can be isolated in a simple way by centrifuging the reaction product to recover a supernatant and isolating the supernatant using ultra-filtration membrane.

DESCRIPTION OF SPECIFIC EMBODIMENTS OF THE INVENTION

Hereinafter, specific embodiments of the present invention are described in detail, including preferred examples and comparative example. However, they are intended to describe the invention in detail such that the invention can be easily practiced by a person with ordinary skill in the technical field to which the invention pertains, and are not intended to mean that the technical idea and range of the present invention are limited thereto.

In accordance with the present invention, the method for isolating a fraction having an anti-inflammatory effect using oyster shell comprises:

1) a preliminary step of removing foreign materials attached to the oyster shell, washing the oyster shell with water and then drying and grinding the washed oyster shell to make a powder;

2) a reaction step of reacting the oyster shell powder obtained from the said preliminary step with an anhydrous citric acid to obtain a reaction product;

3) a supernatant-recovering step of centrifuging the reaction product obtained from the said reaction step to recover a supernatant; and

4) an isolation step of isolating the supernatant obtained from the said supernatant-recovering step using an ultra-filtration membrane and drying the same to isolate a fraction having anti-inflammatory effect.

First, the preliminary step of removing foreign materials attached to the oyster shell, washing the oyster shell with water and then drying the washed oyster shell to make a powder, is conducted. When an oyster shell generated in the oyster farm is collected, various foreign materials are attached to the surface thereof. Therefore, these foreign materials are removed using a knife, etc. Then, the oyster shell is completely washed with water, naturally dried and dry-ground in 50~300 mesh of a suitable size using an air mill in order to facilitate the reaction of the oyster shell with the anhydrous citric acid.

The anhydrous citric acid is added to the oyster shell obtained in the said preliminary step and their reaction is conducted. The reaction step to obtain a reaction product is one of the important steps in the methods for isolating fraction having anti-inflammatory or osteoarthritis-inhibiting effects using oyster shell according to the present invention.

As the reactants to obtain the reaction product of the present invention, anhydrous citric acid has the molecular formulae, $C_6H_8O_7$ or $HOC(CO_2H)(CH_2CO_2H)_2$. When the anhydrous citric acid meets with calcium (Ca), it reacts with the calcium, losing a hydrogen ion ($H^+$), to form a compound called calcium citrate. During this process, water ($H_2O$) and carbon dioxide ($CO_2$) gas are generated. One molecule of citric acid can react with up to three calcium atoms. The chemical formulae associated with this are shown in the following Chemical Formulae (1) to (3):

(1)

(2)

(3)

When all the three calcium are bonded to citric acid, the chemical formula can be expressed as in the following Chemical Formula (4).

(4)

The bonding of calcium and citric acid is a principle wherein citric acid groups surround calcium atoms bonding to calcium to form macromolecules, thereby causing precipitation to occur. Therefore, two citric acid molecules and three calcium carbonates are reacted. The molecular weight of citric acid is 192.12 and the molecular weight of calcium carbonate is 100.09.

To the oyster shell powder obtained in the preliminary step, anhydrous citric acid is added in a ratio of 1:0.1921~1.9212 parts by weight and their reaction is preferably conducted at a relatively low temperature of 4~100° C. for 1~24 hours. Anhydrous citric acid is dissolved in water and used as a citric acid solution. 10 l of 0.1~1.0 M citric acid aqueous solution (0.1921~1.9212 kg of citric acid) is added to 1 kg of oyster shell powder, and they are sufficiently stirred and then reacted.

When the amount of anhydrous citric acid is less than 0.1921 parts by weight, a sufficient reaction with oyster shell does not occur. When the amount of anhydrous citric acid exceeds 1.9212 parts by weight, there occurs a problem that a residual amount of citric acid is generated, thereby lowering the purity of calcium citrate. Furthermore, when the reaction temperature is 4° C. and the reaction time is less than 1 hour, the reaction rate slows, thereby not conducting a sufficient reaction. When the reaction temperature is 100° C. and the reaction time exceeds 24 hours, there occurs a problem that the reaction rate is no longer increased and the energy cost is higher.

In the supernatant-recovering step of centrifuging the reaction product obtained from the said reaction step to recover a supernatant, the oyster shell powder is reacted with citric acid. In the reaction product thus produced, calcium citrate, water, carbon dioxide and the like are mixed. The carbon dioxide is a gas and thus is discharged into the air. The remaining mixed solution is centrifuged to isolate a pellet form of calcium citrate which is the supernatant and the precipitate, thereby recovering the supernatant. At this time, centrifugation is conducted at 8,000 rpm at room temperature for 20 minutes, and then the supernatant and the pellet precipitate are isolated from each other.

The supernatant recovered in the supernatant-recovering step is isolated using an ultrafiltration machine. The ultrafiltration membrane uses two types having cutoff molecular weights of 10 kDa and 3 kDa. Hence, the fraction isolated at more than 10 kDa (below, called "fraction 1"), the fraction isolated between 3 kDa and 10 kDa (below, called "fraction 2") and the fraction isolated at not more than 3 KDa (below, called "fraction 3") are obtained. Subsequently, the fractions 1, 2 and 3 thus obtained can be dried in a vacuum dryer to isolate the fractions.

Further, the method for isolating a fraction having an osteoarthritis-inhibiting effect using oyster shell in accordance with the present invention is compared with the method for isolating a fraction having an anti-inflammatory effect using the oyster shell. The only difference is that the present invention uses only the ultra-filtration membrane with a size of 3 kDa instead of the ultra-filtration membrane with sizes of 10 kDa and 3 kDa to obtain the fraction 3. Therefore, detailed description thereof will be omitted.

Below, the present invention shall be more specifically described through the following examples and comparative examples.

EXAMPLE 1

An oyster shell generated in the oyster farm was collected and various foreign materials attached on the surface thereof were removed. The oyster shell was then completely washed with water, naturally dried and then dry-ground by 50~300 mesh using an air-mill. 0.9606 kg of anhydrous citric acid was dissolved in water to make 10 l of 0.5M citric acid aqueous solution to which 1 kg of oyster shells were added and completely mixed. The mixed solution was then reacted at 30° C. for 12 hours. The resulting reaction product was centrifuged with 8,000 rpm at 4° C. for 20 minutes. The supernatant and the pellet precipitate were isolated from each other. The isolated supernatant was isolated using an ultra-filtration machine. Herein, the ultra-filtration membrane used two types having the fraction molecular weights of 10 kDa and 3 kDa.

The fractions recovered through this process were dried in a vacuum dryer. As a result, the three fractions, i.e., 0.3 g of the fraction 1 (recovery rate 0.014%) isolated at more than 10 kDa, 0.6 g of the fraction 2 (recovery rate 0.029%) isolated between 3 kDa and 10 kDa and 24.5 g of the fraction 3 (recovery rate 2.45%) isolated at not more than 3 kDa were combined to obtain a total of 25.4 g.

EXAMPLE 2

Among the fractions obtained in Example 1, a fraction with a molecular weight of not more than 3 kDa was isolated with ultra-filtration membrane to obtain 24.6 g of the fraction 3.

COMPARATIVE EXAMPLE 1

Indomethacin which is one of the drugs that strongly inhibit cyclo-oxygenase (COX) has an anti-inflammatory activity and so is used mainly for the treatment of osteoarthritis. In the present invention, 35.779 µg of 10 mM indomethacin was used as a comparative drug.

Hereinafter, various experiments were conducted for the fractions 1, 2, 3 and indomethacin obtained in the Examples 1 and 2 and Comparative Example 1.

EXPERIMENT 1

Inhibitory Activity of Cyclo-Oxygenase (COX)-2

In order to simply and rapidly measure the anti-inflammatory activity of the fractions 1, 2 and 3 recovered in Example 1 and indomethacin obtained in Comparative Example 1, the inhibitory activity was measured using COX-2 kit manufactured and sold by US Cayman company. In the experimental method, 10 µl of heme, 10 µl of assay buffer (100 mM Tris-HCl, pH 8.0), and 10 µl of solvent (solvent which dissolved an inhibitor) were added to 2 well of a 96 well plate. For the background well, 10 µl of heme, 10 µl of assay buffer, and 10 µl of solvent were added to 2 wells. For the measurement of 100% initial activity, 10 µl of heme, 10 µl of enzyme (COX-2) and 10 µl of solvent were added to 2 wells. For the measurement of COX inhibitory activity of sample (inhibitor), 10 µl of heme, 10 µl of enzyme (COX-2) and 10 µl of sample were added to 2 wells. As the standard inhibitor, indomethacin was treated by dissolving in dimethyl sulfoxide. The sample was dissolved in 100 mM Tris-HCl (pH 8.0) and then treated according to concentration. 200 µl of assay buffer was added to every well and reacted at room temperature. 10 µl of chemiluminescent substrate was then added to every well with one dispenser using two dispensers to which the emission analyzer was attached. Immediately, 50 µl of arachidonic acid was added using another dispenser and then the relative luminescence unit (RLU) was measured with a luminescence analyzer.

As a result, the COX-2 inhibitory activity was identified as 79% for 10 mM indomethacin, 25% for the fraction 1, 7% for the fraction 2 and 42% for the fractions 3 as shown in Table 1. It has been identified that the fractions 1 and 3 of Example 1 exhibit a high COX-2 inhibiting activity even at a low concentration as compared with indomethacin of Comparative Example 1. In particular, the fraction 3 of the fractions exhibited the most excellent activity.

TABLE 1

Inhibitory Activity of Cyclo-oxygenase (COX)-2

|  | Concentration (µg) | COX-2 inhibitory activity (%) |
|---|---|---|
| Comparative Example 1 | 35.779 | 79 ± 12 |
| Example 1, Fraction 1 | 10.0 | 25 ± 9 |
| Example 1, Fraction 2 | 10.0 | 71 ± 12 |
| Example 1, Fraction 3 | 10.0 | 42 ± 18 |

*All experimental date were mean ± SD of triple determinations

EXPERIMENTAL EXAMPLE 2

Anti-inflammatory effect of the fraction 3 from Raw 264.7 macrophages induced by LPS (1) Measurement of Nitric Oxide (NO) Yield The cells were injected by $2\times10^4$ cells/ml per well in 96-well plate and incubated for 2 hours. The fraction 3 of Example 2 was treated according to concentration and incubated for 2 hours. Lipo poly saccharide (LPS) was added in an amount of 1 µg/ml to induce a stress. After incubation for 20 hours, the supernatant was taken and measured. The NO content of the supernatant was measured by Griess reaction. To 50 µl of the supernatant, the same amount of the Griess reagent, i.e., 0.1% N-(1-naphthyl)-ethylenediamine, 1% sulfanilamide in 5% phosphoric acid] was introduced, agitated, and incubated at room temperature for 10 minutes. The absorbance at 550 nm was measured and the results are shown in Table 2 below. When only one cell was incubated and the NO yield was considered to be 100%, the cells treated with LPS were stimulated, thus increasing the NO yield to 196.7%. The NO yields increased through LPS stimulation were measured as 125%, 120%, 110%, 101.7%, respectively, at the treatment concentration 10~100 µg/ml of fraction 3. Therefore, it can be seen that as the concentration increased, the NO yield significantly decreased (p<0.05).

(2) Measurement of Reactive Oxygen Standard (ROS Level) in Cells

Figure 1:
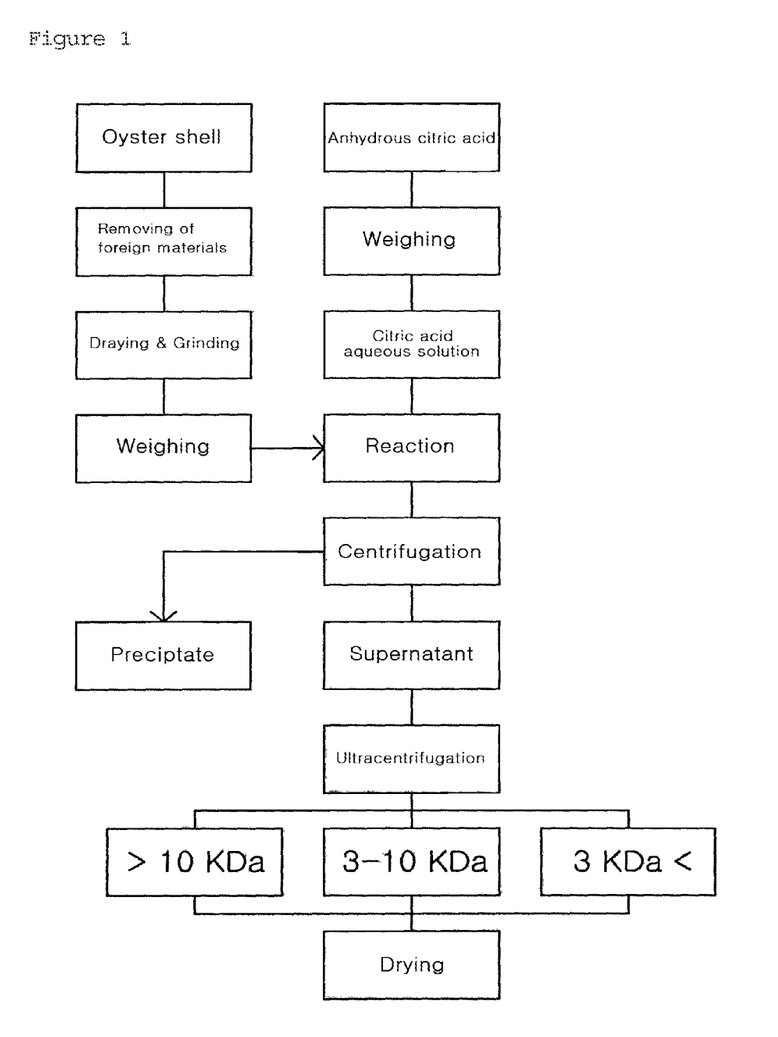
FIG. 1 is a schematic process diagram for the method for isolating fraction having anti-inflammatory or osteoarthritis-inhibiting effects using oyster shell in accordance with the present invention.
Figure 2:
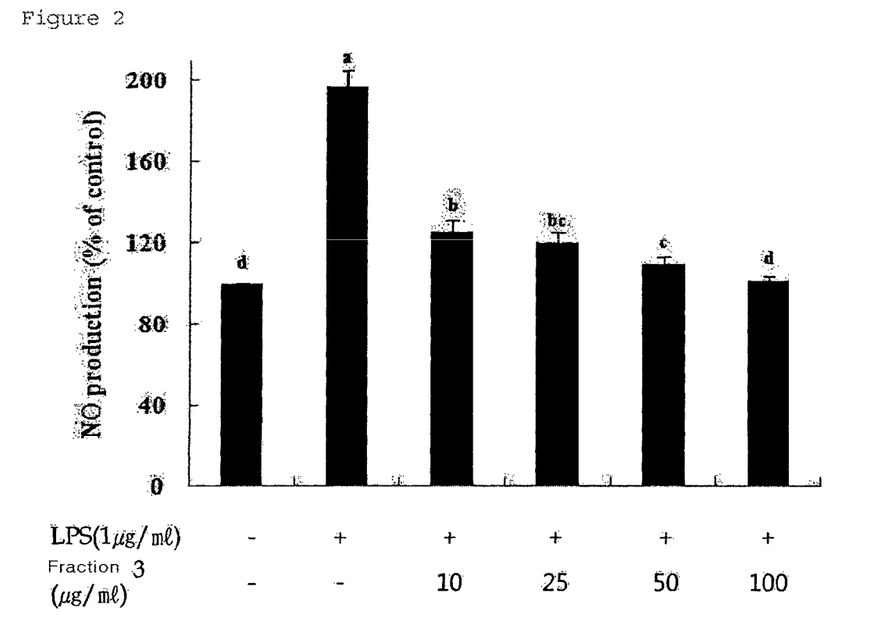
FIG. 2 is a graph showing the results of analysis of the NO producing effect of the fraction 3 recovered from Example 1 of the present invention.
Figure 3:
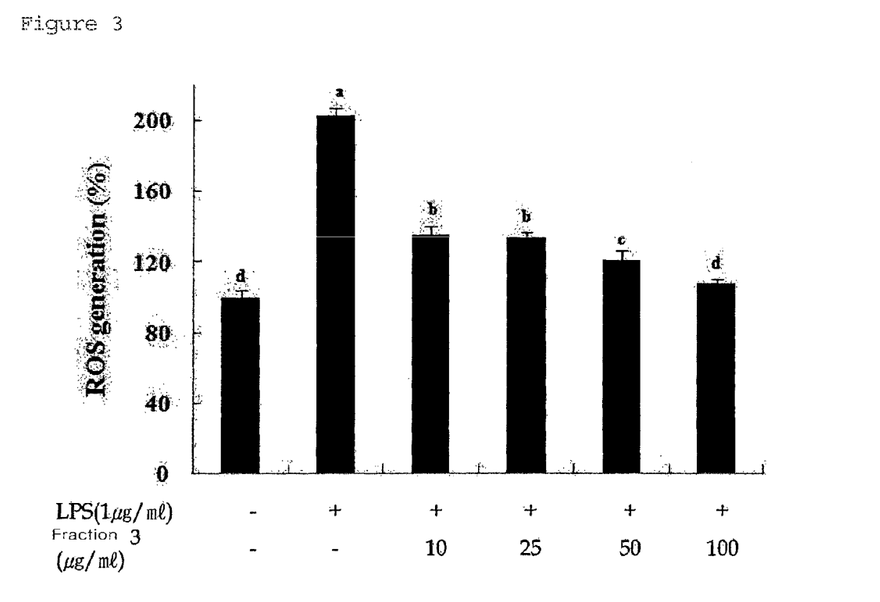
FIG. 3 is a graph showing the results of analysis of the active oxygen generation rate in cells of the fraction 3 recovered from Example 1 of the present invention.

Dichlorofluorescein diacetate (DCF-DA) was measured by a principle wherein acetyl group was removed in cells and quantitatively reacted with an intracellular radical (mainly, hydrogen peroxide) to change to DCF fluorescence material. DCF-DA measures the generation of reactive oxygen in the oxidative stress. If the cells were in the confluence state, the cells were seeded with 2×104 cells/ml per well in a 96-well plate and incubated for 2 hours. The samples were then treated according to concentration and incubated for 2 hours to which LPS (1 µg/ml) was added and incubated for 20 hours, thus inducing stress. The culture media was then removed and the cells were washed twice in phosphate buffered saline (PBS). The cells were introduced with 100 µM of DCF-DA, incubated for 15 minutes and again incubated at room temperature for 60 minutes. The rate of increase of DCF-DA fluorescence was measured by flow cytometer. The results are shown in FIG. 3.

The reactive oxygen yield induced by LPS in RAW 264.7 macrophage was 202.3%. When the fraction 3 was pre-treated in a concentration of 10~100 μg/ml, the reactive oxygen yield was decreased in a concentration-dependent manner. In particular, at the concentration of 100 μg/ml, the reactive oxygen yield was 107.8% which does not represent a significant difference ($p<0.05$) as compared with the control group, thus leading to a high reactive oxygen yield.

(3) Measurement of Lipid Peroxide

The degree of lipid peroxidation was measured according to Fraga method by thiobarbituric acid reactive substance yield (TBARS). In 96-well plate, the cells were introduced by 2×10⁴ cells/ml per well and incubated for 2 hours. The samples were treated according to concentration and incubated for 2 hours. LPS (1 μg/ml) was then added to induce a stress. After the incubation for 20 hours, 200 μl of media supernatant per well was put in a corning tube and incubated for 1 hour to which 400 μl of TBARS solution was added, agitated and then boiled at 95° C. for 20 minutes. After cooling and mixing again, the absorbance at 532 nm was measured with the supernatant which was centrifuged at 4,000 rpm for 10 minutes. Lipid peroxides were calculated by converting into the amount of malonic dialdehyde (MDA).

Figure 4:
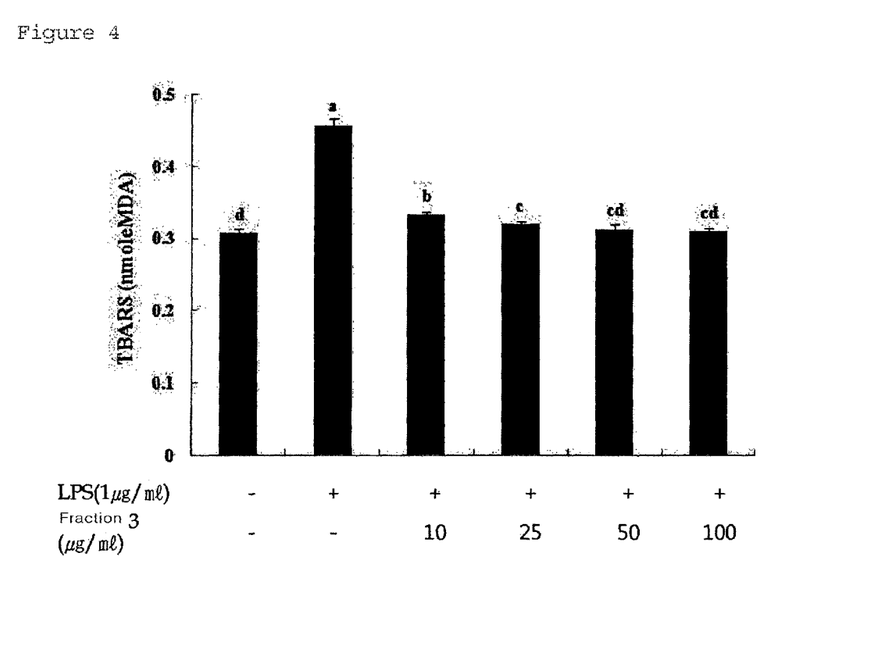
FIG. 4 is a graph showing the results of analysis of the influence on the lipid peroxidation level of the fraction 3 recovered from Example 1 of the present invention.

If the fraction 3 was treated by inducing stress with LPS in RAW 264.7 cells, the influence on the degree of lipid peroxidation was investigated. The results were shown in FIG. 4. As a result, it can be seen that the TBARS yield in 10~50 μg/ml concentration of the fraction 3 was significantly decreased in a dose-dependent manner.

EXPERIMENTAL EXAMPLE 3

Inhibitory Effects of Arthritis in Animal Models of Osteoarthritis (1) Experiment Animals and Breeding 40 eight week-old animal models of osteoarthritis C57BL/6J mouse were purchased from Central Laboratory Animal Inc. (Seoul, Korea), adapted with a general diet for 1 week and then used in the experiments. The temperature and humidity of the breeding room were maintained at 20±2° C., 50±10%, the lightening conditions were such that the light was turned on and off every 12 hours and the light was kept on from 07:00~19:00. During the experiment, the feedstuff (Orient Bio, Seoul, Korea) and water were to be freely taken.

(2) Preparation of Model of Osteoarthritis

The osteoarthritis was induced by the method given in the test guidelines of the effect of the herbal preparation presented by the Korean Food and Drug Administration. Papain (type IV, double crystallized, 15 units/mg, Sigma, USA) was adjusted to a concentration of 1.0% (w/v) in which 0.03 ML-cystein HCl (Sigma, USA) was supplemented for the activation of papain and then passed through the patellar ligament. Physiological saline 6 was administered in the right knee joint to induce osteoarthritis.

(3) Classification of Experiment Group

The experiment animals were adapted in a lab environment for 1 week and then the body weight was measured. Eight animals were assigned to each group to have even body weight. In the normal group, the physiological saline 6 was injected in the right knee joint and then the physiological saline 0.2 ml was orally administered once a day for 20 days. In the treated groups, i.e., a control group, a drug-administered group and a fraction 3-administered group, papain 6 was injected in the right knee joint to induce osteoarthritis. The physiological saline in the control group, Diclofenac sodium (DS, 2 mg/kg/bw) in the drug-administered group, and 100 mg/kg/bw {below, called "fraction 3 (100)"} and 200 mg/kg/bw {below, called "fraction 3 (200)"} in the fraction 3-administered group of Example 2 were orally administered once daily at a predetermined time for 20 days.

(4) Sample Treatment

All subjects were lightly anesthetized with ether at the experiment end day to take a heart blood sample. The blood was centrifuged to isolate a serum. Immediately after taking a heart blood sample, the right hip joint and ankle joint were isolated and removed so as not to damage the knee joint. The tibial of the right knee joint was fixed in 10% neutral formalin solution for 24 hours and then used for the visual observation of the joints.

(5) Visual Observation

Figure 5:
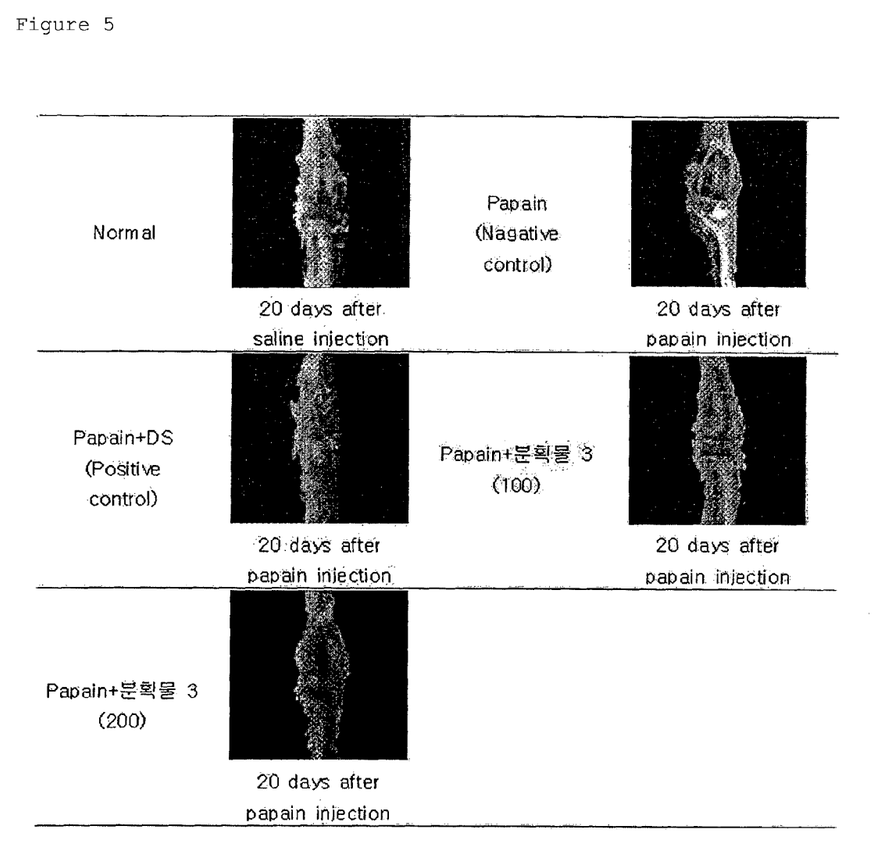
FIG. 5 is a photograph showing the results of analysis of the inter-group differences in the knee joint surfaces according to the present invention.

The cartilage surrounding the fixed right knee joint was cleaned to take a picture. The damage level of the joint cartilage surface was visually confirmed. The difference between the groups for the knee joint surfaces is shown in FIG. 5. The knee joint of the normal group has a smooth surface and shows a normal structure, while the papain-administered control group has a rough knee joint surface and is lusterless. Depending on the site, the color of the cartilage was changed and the elimination of the cartilage surface was observed in irregular shapes, which exhibited an abnormal structure.

The DS-treated group exhibited a visual appearance similar to that of the papain-administered group, but the scope of the discoloration was less and the elimination of visual cartilage surface was not observed. The fraction 3-treated group exhibited a reduced scope of discoloration and an increased luster of the surface as compared with a papain-administered group. Such a visual diagnosis was similar to that for the DS-treated group.

(6) Evaluation of Osteoarthritis Index

The osteoarthritis index for the observed histopathological lesions in the articular cartilage and synovial membrane was digitalized in accordance with a method of Rudolphi, at al. and is shown in Table 2 below.

TABLE 2

| Matrix Structure | | Cellularity | |
|---|---|---|---|
| 0 | Normal | 0 | Normal |
| 1 | Surface irregularities | 2 | Reduced |
| 3 | Superficial fibrillation | 5 | Strongly reduced |
| 6 | Clefts in deep zone | 8 | Total loss of cartilage and cells |
| 8 | Massive loss of cartilage | | |
| Subchondral Bone | | Synovial Membrane | |
| 0 | Normal | 0 | Normal |
| 3 | Remodeling processes | 3 | Mild hyperplasia |
| 8 | Thickening strong sclerosis | 5 | Severe hyperplasia |
| | | 8 | Hyperplasia with infiltration of inflammatory cells |

The osteoarthritis index according to the histopathological opinions per subject observed in the papain-administered group and treated group is shown in Table 3. The DS-treated group and the fraction 3-treated group exhibited a significantly lower osteoarthritis index ($p<0.05$) than the papain-administered control group. The fraction 3 (200)-treated group had a lower osteoarthritis index than the fraction 3 (100)-treated group, but there was no significant difference.

TABLE 3

The osteoarthritis index according to histopathological opinions per subject

| Group and Identification No. | | Matrix structure | Cellularity | Subchondral bone | Synovial membrane | Sum of osteoarthric score |
|---|---|---|---|---|---|---|
| Papain | 1 | 3 | 5 | 8 | 8 | 24 |
|  | 2 | 3 | 5 | 3 | 5 | 16 |
|  | 3 | 8 | 2 | 0 | 0 | 10 |
|  | 4 | 6 | 5 | 3 | 8 | 22 |
|  | 5 | 8 | 5 | 0 | 5 | 18 |
|  | 6 | 3 | 8 | 3 | 8 | 22 |
|  | 7 | 3 | 8 | 8 | 8 | 27 |
|  | 8 | 6 | 2 | 8 | 3 | 19 |
|  | Mean | 5.0 | 5.0 | 4.1 | 5.6 | 19.8 |
| Papain + DS | 1 | 1 | 2 | 3 | 0 | 6 |
|  | 2 | 1 | 2 | 0 | 1 | 4 |
|  | 3 | 3 | 2 | 3 | 3 | 11 |
|  | 4 | 3 | 2 | 0 | 0 | 5 |
|  | 5 | 3 | 2 | 0 | 3 | 8 |
|  | 6 | 6 | 2 | 0 | 3 | 11 |
|  | 7 | 3 | 2 | 3 | 0 | 8 |
|  | 8 | 1 | 2 | 0 | 3 | 6 |
|  | Mean | 2.6 | 2.0 | 1.1 | 1.5 | 7.4 |
| Papain + Fraction 3 (100) | 1 | 3 | 2 | 0 | 3 | 8 |
|  | 2 | 6 | 5 | 3 | 5 | 19 |
|  | 3 | 3 | 2 | 3 | 3 | 11 |
|  | 4 | 3 | 2 | 3 | 3 | 11 |
|  | 5 | 6 | 5 | 5 | 3 | 19 |
|  | 6 | 8 | 5 | 3 | 3 | 19 |
|  | 7 | 3 | 2 | 3 | 3 | 11 |
|  | 8 | 5 | 5 | 3 | 3 | 16 |
|  | Mean | 4.6 | 3.5 | 2.9 | 3.3 | 14.3 |
| Papain + Fraction 3 (200) | 1 | 1 | 2 | 0 | 3 | 6 |
|  | 2 | 3 | 2 | 3 | 3 | 11 |
|  | 3 | 1 | 0 | 0 | 3 | 4 |
|  | 4 | 6 | 2 | 3 | 4 | 14 |
|  | 5 | 8 | 5 | 3 | 3 | 19 |
|  | 6 | 6 | 2 | 3 | 0 | 11 |
|  | 7 | 3 | 0 | 3 | 3 | 9 |
|  | 8 | 6 | 5 | 3 | 5 | 19 |
|  | Mean | 4.3 | 2.3 | 2.3 | 3.1 | 11.6 |

(7) Measurement of Cytokine Content in Blood

The contents of tumor necrosis factor-α (TNF-α), interleukin-1β (IL-1β) and interleukin-6 (IL-6) were measured using enzyme-linked immunosorbent assay (ELISA) kit, respectively.

① TNF-α Content in Blood

Figure 6:
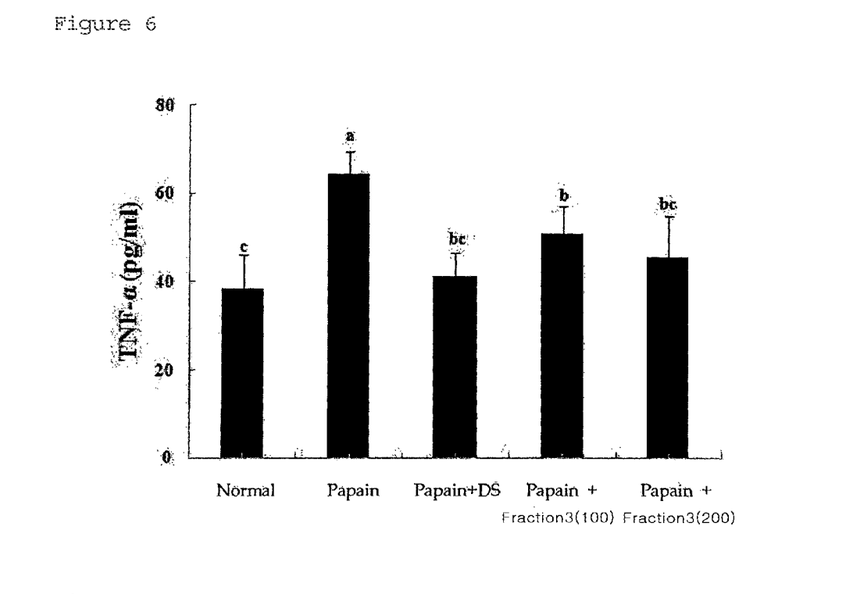
FIG. 6 is a graph showing the results of the measurement of the inflammatory cytokine TNF-α content according to the present invention.

The effect of fraction 3 of the inflammatory cytokine TNF-α produced in large quantities in animals where arthritis was induced by injection of papain, was measured by ELISA method. The measured results are shown in FIG. 6. TNF-α content in blood for the papain-administered group was significantly higher than that for the normal group. DS and fraction 3-treated groups were significantly lower than the papain-administrated control group. In particular, the fraction 3 (200)-treated group exhibited a low TNF-α content similar to that of the DS-treated group, and also was significantly lower ($p<0.05$) as compared with that of the fraction 3 (100)-treated group.

② Interleukin-1β Content in Blood

Figure 7:
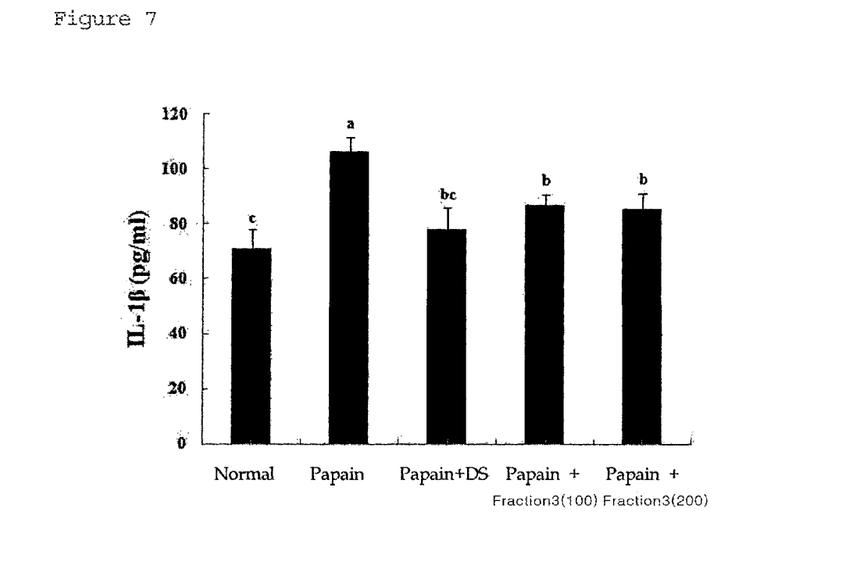
FIG. 7 is a graph showing the results of the measurement of the inflammatory cytokine IL-1β content according to the present invention.
Figure 8:
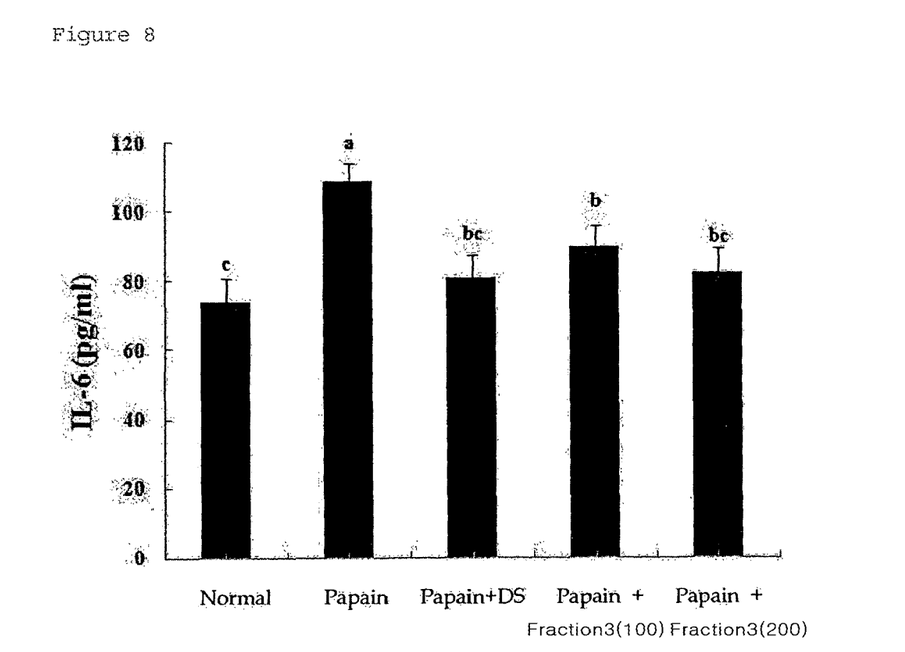
FIG. 8 is a graph showing the results of the measurement of inflammatory cytokine IL-6 content according to the present invention.

The effect of fraction 3 of the inflammatory cytokine IL-1β produced in large quantities in animals where arthritis was induced by injection of papain was measured by ELISA method. The measured results are shown in FIG. 7. IL-1β content in blood for the papain-administered group was significantly higher than that of the normal group. DS and fraction 3-treated groups were significantly lower ($p<0.05$) than the papain-administrated control group. The fraction 3 (200)-treated group exhibited a lower IL-1β content than that of the fraction 3 (100)-treated group, but there was no significant difference.

③ Interleukin-6 Content in Blood

The difference of IL-6 content in mice where arthritis was induced by papain injection is shown in Table 8 below. IL-6 content in blood in the papain-administered group is significantly higher than that in the normal group. DS and fraction 3-treated groups are significantly lower than the papain-administrated control group. In particular, the fraction 3 (200)-treated group exhibited a significantly lower IL-6 content ($p<0.05$) than the fraction 3 (100)-treated group.

What is claimed is:

1. A method for isolating a fraction having an anti-inflammatory effect using oyster shell, characterized in that the said method comprises:
    a) a preliminary step of removing foreign materials attached to the oyster shell, washing the oyster shell with water and then drying and grinding the washed oyster shell to make a powder;
    b) a reaction step of reacting the oyster shell powder obtained from the said preliminary step with an anhydrous citric acid to obtain a reaction product;
    c) a supernatant-recovering step of centrifuging the reaction product obtained from the said reaction step to recover a supernatant; and
    d) an isolation step of isolating the supernatant obtained from the said supernatant-recovering step using ultra-filtration membrane and then drying the same to isolate a fraction having an anti-inflammatory effect.

2. The method for isolating a fraction having an anti-inflammatory effect using oyster shell according to claim 1, characterized by adding an anhydrous citric acid to the oyster shell powder during the reaction step in a ratio of 1: 0.1921~1.9212 parts by weight and conducting the reaction at 4~100° C. for 1~24 hours.

3. The method for isolating a fraction having an anti-inflammatory effect using oyster shell according to claim 2, characterized in that, in the said supernatant-recovering step, the ultra-filtration membrane has a size of 10 kDa.

4. The method for isolating a fraction having an anti-inflammatory effect using oyster shell according to claim 2, characterized in that, in the said supernatant-recovering step, the ultra-filtration membrane has a size of 3 kDa.

5. A method for isolating a fraction having an osteoarthritis-inhibiting effect using an oyster shell, characterized in that the said method comprises:
    a) a preliminary step of removing foreign materials attached to the oyster shell, washing the oyster shell with water and then drying and grinding the washed oyster shell to make a powder;
    b) a reaction step of adding anhydrous citric acid to the oyster shell powder obtained from the said preliminary step in a ratio of 1: 0.1921~1.9212 parts and conducting the reaction at 4~100° C. for 1~24 hours;
    c) a supernatant-recovering step of centrifuging the reaction product obtained from the said reaction step to recover a supernatant; and
    d) an isolation step of isolating the supernatant obtained from the said supernatant-recovering step using ultra-filtration membrane having a size of 3 KDa and then drying the same to isolate a fraction having an osteoarthritis-inhibiting effect.

* * * * *

UNITED STATES PATENT AND TRADEMARK OFFICE
CERTIFICATE OF CORRECTION

| | |
|---|---|
| PATENT NO. | : 9,937,210 B2 |
| APPLICATION NO. | : 14/429321 |
| DATED | : April 10, 2018 |
| INVENTOR(S) | : Hak-Ju Kim et al. |

Page 1 of 1

It is certified that error appears in the above-identified patent and that said Letters Patent is hereby corrected as shown below:

On the Title Page

Item (30) Foreign Application Priority Data
Insert the following:
--Sep. 18, 2012 (KR)................. 10-2012-0103334--

Signed and Sealed this
Twenty-fifth Day of September, 2018

Andrei Iancu
*Director of the United States Patent and Trademark Office*